(12) United States Patent
Khalili et al.

(10) Patent No.: US 11,426,182 B2
(45) Date of Patent: Aug. 30, 2022

(54) BLADE REAMER ASSEMBLY FOR SURGICAL USE

(71) Applicant: Razor Medical Instruments, Inc., Portsmouth, NH (US)

(72) Inventors: Farid Bruce Khalili, Briarcliff Manor, NY (US); James T. Caillouette, Newport Beach, CA (US)

(73) Assignee: RAZOR MEDICAL INSTRUMENTS, INC., Portsmouth, NH (US)

( * ) Notice: Subject to any disclaimer, the term of this patent is extended or adjusted under 35 U.S.C. 154(b) by 295 days.

(21) Appl. No.: 16/859,447

(22) Filed: Apr. 27, 2020

(65) Prior Publication Data

US 2020/0253620 A1 Aug. 13, 2020

Related U.S. Application Data

(62) Division of application No. 16/131,642, filed on Sep. 14, 2018, now Pat. No. 10,631,883.

(60) Provisional application No. 62/561,652, filed on Sep. 21, 2017.

(51) Int. Cl.
A61B 17/16 (2006.01)

(52) U.S. Cl.
CPC ...... *A61B 17/1659* (2013.01); *A61B 17/1666* (2013.01)

(58) Field of Classification Search
CPC .................. A61B 17/1666; A61B 17/1659
See application file for complete search history.

(56) References Cited

U.S. PATENT DOCUMENTS

| | | | | |
|---|---|---|---|---|
| 2,785,673 A | * | 3/1957 | Anderson | A61F 2/3601 623/23.11 |
| 3,605,527 A | * | 9/1971 | Gambale | A61B 17/1666 76/115 |
| 4,621,637 A | * | 11/1986 | Fishbein | A61B 17/1666 606/81 |
| 7,837,686 B1 | | 11/2010 | Tulkis | |

(Continued)

FOREIGN PATENT DOCUMENTS

| | | |
|---|---|---|
| EP | 3468489 A1 | 4/2019 |
| WO | 2007003243 A1 | 1/2007 |

OTHER PUBLICATIONS

Extended European Search Report issued in corresponding EP Application No. 18857555.9, dated Sep. 30, 2021.

(Continued)

*Primary Examiner* — Christian A Sevilla
(74) *Attorney, Agent, or Firm* — McDermott Will & Emery LLP

(57) ABSTRACT

A device is provided, including a cutting rib, the cutting rib including an arcuate portion having an outer sharp edge and a centralizer configured to receive the cutting rib through a radial slot, the radial slot forming a gap with the cutting rib. The arcuate portion of the cutting rib is formed into a profile that follows a surface of the centralizer, the outer sharp edge of the arcuate portion of the cutting rib has a wavy profile that forms a tunnel in the gap between the centralizer and the cutting rib, and the outer sharp edge of the arcuate portion of the cutting rib protrudes outwardly from the surface of the centralizer. A method for using the device to cut bone in a surgical configuration is also provided.

17 Claims, 10 Drawing Sheets

(56) References Cited

U.S. PATENT DOCUMENTS

| | | | |
|---|---|---|---|
| 2004/0039451 A1* | 2/2004 | Southworth | A61B 17/1668 623/23.46 |
| 2006/0129157 A1* | 6/2006 | Desarzens | A61B 17/1666 606/81 |
| 2011/0202060 A1 | 8/2011 | White et al. | |
| 2012/0191099 A1 | 7/2012 | Victor | |
| 2013/0204254 A1* | 8/2013 | Slone | A61B 17/1666 264/250 |
| 2016/0089156 A1 | 3/2016 | Fortin et al. | |
| 2017/0035443 A1 | 2/2017 | Sausen et al. | |

OTHER PUBLICATIONS

International Preliminary Report on Patentability for PCT/US2018/051092 dated Mar. 24, 2020, in 9 pages.
Kim, Y.S., et al. "Fracture of the acetabulum during insertion of an oversized hemispherical component", J. Bone Joint Surg. Am. Jan. 1995:77(1):111-7. PubMed PMID: 7822342.
Martin, C.T., et al. "Protrusio after Medical Acetabular Wall Breach in Total Hip Arthroplasty.", Iowa Ortho J. 2015; 35:99-107.
International Search Report for PCT/US2018/051092 dated Dec. 31, 2018, 4 pages.
Written Opinion for PCT/US2018/051092, dated Dec. 31, 2018, 8 pages.

* cited by examiner

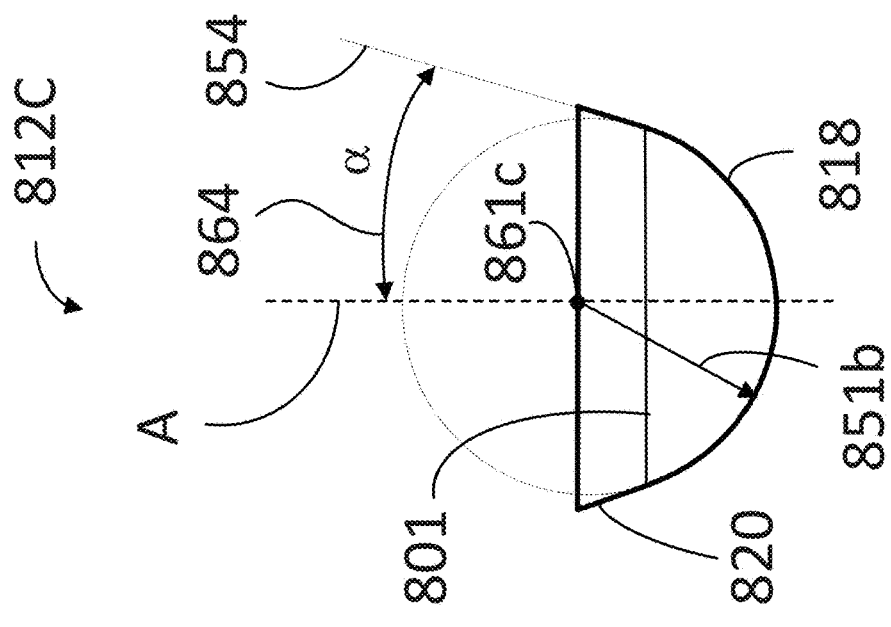
FIG. 8C
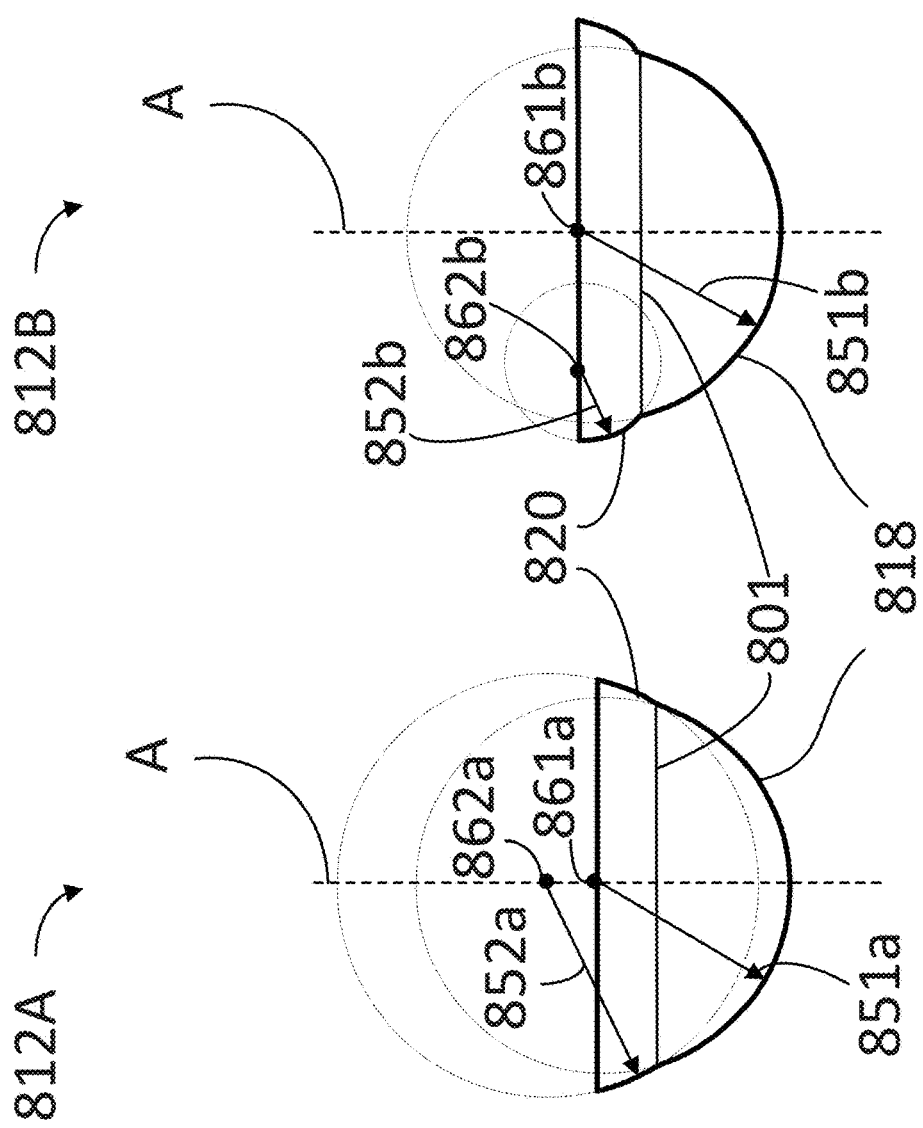
FIG. 8B
FIG. 8A

BLADE REAMER ASSEMBLY FOR SURGICAL USE

CROSS-REFERENCE TO RELATED APPLICATIONS

The present application is related to, and claims the benefit of priority under 35 U.S.C. § 119(e) from, U.S. Provisional Patent Application, U.S. 62/561,652, entitled BLADE REAMER ASSEMBLY FOR SURGICAL USE, to Farid Bruce Khalili, filed on Sep. 21, 2017, and under 35 U.S.C. § 121 as a divisional application of U.S. Ser. No. 16/131,642, entitled BLADE REAMER ASSEMBLY FOR SURGICAL USE, and filed on Sep. 14, 2018, to Farid Bruce Khalili et al., the contents of which applications are herein incorporated by reference in their entirety, for all purposes.

BACKGROUND

Disclosed herein are systems and methods that relate to tools used for cutting bone during joint replacement surgery. One particular application is for a rib assembly to be used for cutting the cavity of the acetabulum when replacing the hip joint by a prosthetic cup. Other examples are patella resurfacing ribs, ribs used to plane the calcar when implanting a femoral component of a total hip replacement, and axial tapered or cylindrical long ribs used in hip or knee replacement used to find and shape the femoral canal and glenoid reamers that are used in shoulder arthroplasty.

SUMMARY

A number of shortcomings exist with the use of blunt reamers that are used in many procedures. One shortcoming with blade-type reamers is occasional chatter and vibration. Chatter is noticed in early stages of cutting, usually during the first few seconds of reaming after the reamer engages the bone. As a result of chatter and vibration, a wavy surface finish is noticed in the socket, usually noticeable along a perimeter of the socket. This embodiment introduces an improved blade-type reamer assembly that substantially reduces chatter and vibration during surgical use.

In some embodiments described herein, a device includes a cutting rib, the cutting rib including an arcuate portion having an outer sharp edge and a centralizer configured to receive the cutting rib through a radial slot, wherein the radial slot forms a gap with the cutting rib. The arcuate portion of the cutting rib is formed into a profile that follows a surface of the centralizer, the outer sharp edge of the arcuate portion of the cutting rib has a wavy profile that forms a tunnel in the gap between the centralizer and the cutting rib, and the outer sharp edge of the arcuate portion of the cutting rib protrudes outwardly from the surface of the centralizer.

In some embodiments, a method includes joining a cutting rib and a centralizer to form a cutting assembly, and joining the cutting assembly to a reamer handle. The method also includes providing a rotating motion to the cutting rib assembly through the reamer handle, removing a substrate material by contacting the cutting assembly with a substrate, and adjusting the rotating motion of the cutting rib assembly through the reamer handle according to a substrate condition.

In some embodiments, the centralizer includes a first portion consistent with a first spherical surface having a first radius and a second portion consistent with a second spherical surface having a second radius. In some embodiments, the first radius is different from the second radius. Some embodiments include a cap coupled with a distal tip of the centralizer to limit access of a distal portion of the cutting rib to a substrate. In some embodiments, the centralizer includes a frusto-conical surface portion at a distal end to reduce a reach depth of the cutting rib into a substrate.

BRIEF DESCRIPTION OF THE DRAWINGS

FIGS. 8A-C illustrate views of a centralizer with several configurations of multi-curve profiles, according to some embodiments.

DETAILED DESCRIPTION OF THE FIGURES

Described herein is a selectively disposable reamer assembly for cutting and shaping of bone for implantation of a medical device. The cutter assembly is directly attached to the reamer handle. The reamer handle directly delivers torque to the ribs. Bone cutting edges of each of the ribs may have a rake and are sharpened to cut and shape bone surfaces when rotated and pushed against the bone. The assembly has two, three, or a few more components, including a series of unitized cutting ribs that are selectively disposable, which are assembled to a centralizer that is selectively disposable. Some embodiments include an additional piece, which is a distal cap (e.g., a "plug") that can be selectively attached to the distal end of the first assembly and has the same or larger outer diameter as the ribs.

In some applications, the floor (medial wall) of the acetabular socket of a patient may be thin and the surgeon may elect not to remove bone from the medial wall. Accordingly, it is desirable to avoid inadvertent reaming through the medial wall of the acetabulum. Over-reaming the medial acetabular wall results in loss of supportive bone stock and has been proposed to be a significant risk factor for Medial acetabular prosthesis migration, which is a complication of total hip arthroplasty. Christopher Martin et al. investigated the effect on load-to-failure strength of up to a 2 cm defect in the medial acetabular wall caused by over-reaming in a cadaveric model. Nine human fresh-frozen hemi-pelvises were over-reamed to create the defect, implanted with acetabular cups, and then loaded to failure. The nine contralateral hemi-pelvises were reamed line-to-line and served as a control. The authors also investigated the ability of acetabular screws to restore strength to the construct. Testing showed that over-reaming decreased the load to failure strength by a mean of 23% (4816 v. 3675 N, p=0.0024). The addition of two acetabular screws did not successfully restore the strength of the construct. (Protrusio after Medial Acetabular Wall Breach in Total Hip Arthroplasty. Christopher Martin, Anneliese D. Heiner, PhD, Andrew James Pugely, MD, Yubo Gao1, Thomas E. Baer, PhD, Nicolas Noiseux, MD. J Bone Joint Surg Am, 77(1): 111-7, 1995).

Figure 1:
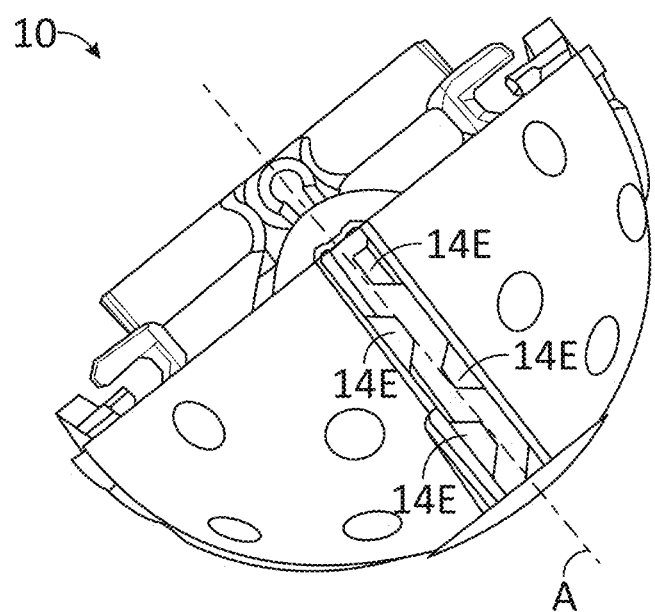
FIG. 1 illustrates a perspective view of the selectively disposable rib assembly, according to some embodiments.
Figure 1:
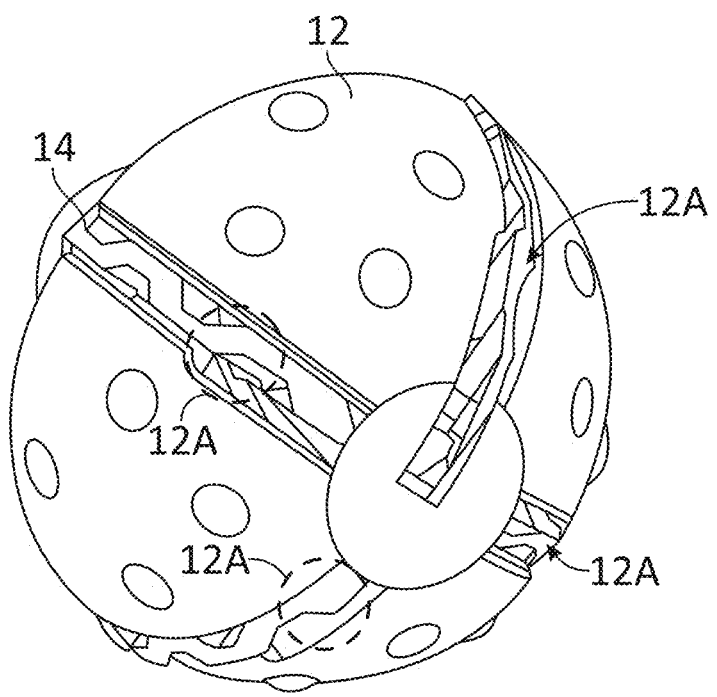

FIG. 1 is a perspective view of the selectively disposable cutting rib assembly 10 of the embodiment. Cutting rib assembly 10 includes a centralizer 12, cutting ribs 14. Centralizer 12 includes radial slots 12A into which cutting ribs 14 may fit. In some embodiments, cutting rib 14 has a wavy profile that forms tunnels 14E in the gap between centralizer 12 and cutting rib 14. Tunnels 14E enable the passage of bone chips or substrate debris. Tunnels 14E allow for passage of bone chips and loose tissue through the slots into the centralizer, which would then accumulate within the centralizer basket. The substrate debris (e.g., bone chips) may be used as auto graft to fill bone cavities, when desired. In some embodiments, cutting ribs 14 are rigid enough for cutting bone. In some embodiments, centralizer 12 is concentric with cutting ribs 14, allowing an even bone removal. In some embodiments, centralizer 12 includes a frusto-conical surface portion at a distal end, to reduce a reach depth of the cutting rib 14 into a substrate (e.g., bone, or any other hard tissue material). In some embodiments, cutting rib assembly 10 includes three or more cutting ribs 14, wherein an outer edge of each cutting rib 14 is sharpened on the side that will be in contact with the substrate.

In medical applications, centralizer 12 correctly positions cutting ribs 14 within a bone cavity so bone is removed to the limit allowed around the diameter of centralizer 12. Centralizer 12 also limits the range within which cutting ribs 14 can remove or cut bone. Once cutting rib assembly 10 is rotating and placed within the cavity and a force is applied (e.g., by a surgeon), the sharp edge of the blades in cutting ribs 14 may get embedded into the cartilage and/or bone, forming a groove or a groove-like depression in the tissue. The surgeon activates a powered reamer driver that sets cutting rib assembly 10 into a rotatory movement about symmetry axis 'A.' Centralizer 12 mitigates the effect of "kicks" and "jerks" of the cutting rib assembly 10 when cutting rib 14 climbs out of the embedded position, or groove, on the substrate. Cutting rib 14 continues to fall in and climb out of the grooves throughout the entire reaming process and may even create new grooves as a force is applied. This jerking motion may cause uneven cutout surface, chatter and vibration, which are damped by centralizer 12. Centralizer 12 substantially reduces the depth that the sharp edges of cutting ribs 14 penetrate the bone. In some embodiments, centralizer 12 has a concave, hollow shape that acts as a basket that collects substrate debris (e.g., cut bone and tissue), enabling the removal of the debris from the substrate-cutting rib assembly interface. This further enables a smooth cutout surface on the substrate.

In some embodiments, centralizer 12 may be assembled onto cutting ribs 14 to form cutting rib assembly 10. Cutting rib assembly 10 moves as a rigid, or semi-rigid body. In one embodiment, the surgeon or operator can detach centralizer 12 from cutting rib assembly 10, as desired. For example, in some embodiments the surgeon may be interested in sharpening, repairing, cleaning, or replacing at least one of cutting ribs 14, and thus detach centralizer 12 and cutting ribs 14 from cutting rib assembly 10. In some embodiments, the surgeon may desire to clean the debris accumulated inside centralizer 12. A cap 15 can be attached to the tip of cutting rib assembly 10 when cutting ribs 14 are assembled with centralizer 12. In some embodiments, centralizer 12 includes a shell component with correspondingly shaped outer convex and inner concave surfaces.

Figure 2:
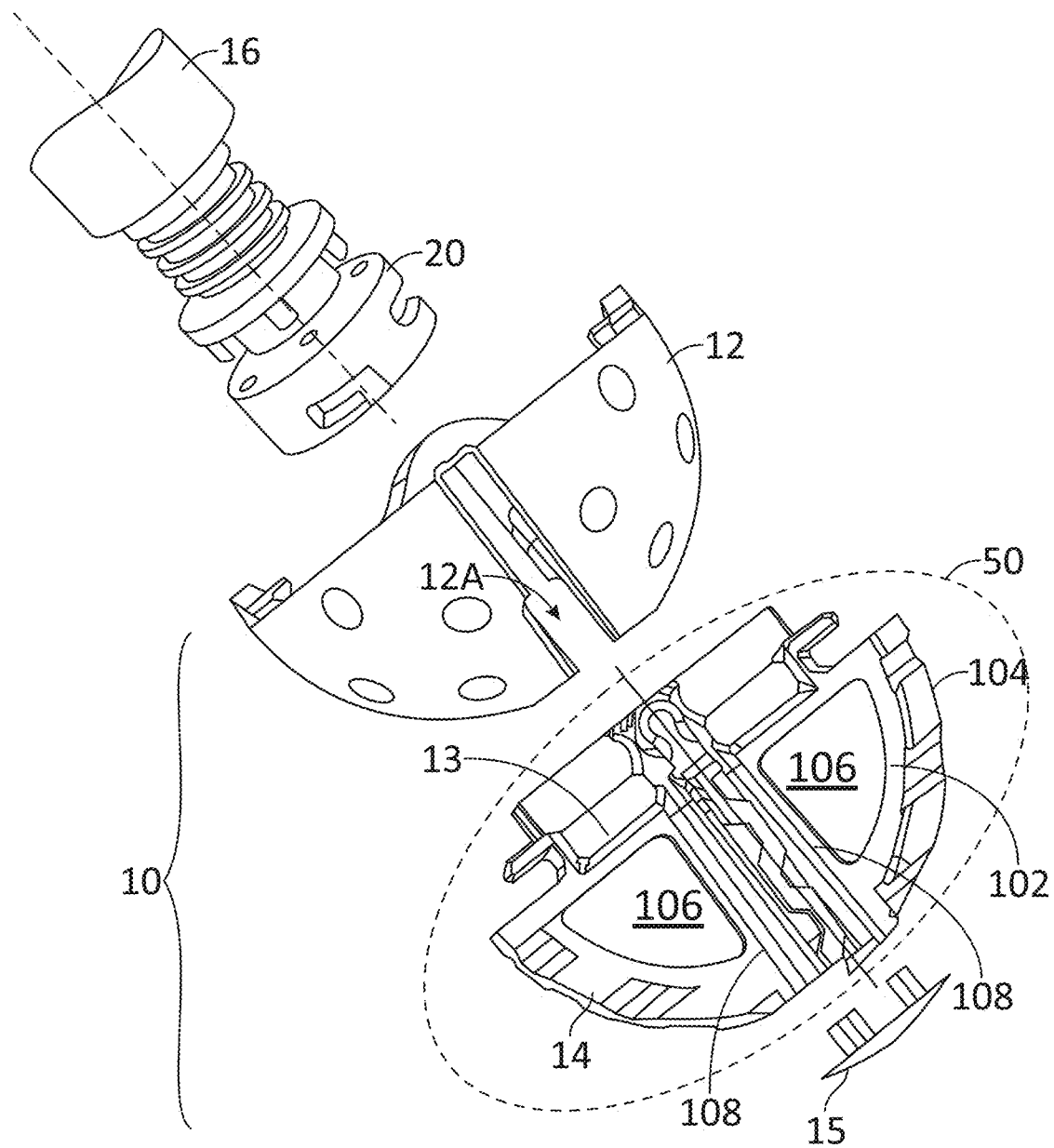
FIG. 2 illustrates an exploded view of the reamer handle, centralizer, rib, and distal plug, according to some embodiments.

FIG. 2 illustrates an exploded view of a centralizer 12, a cutting rib 14, and a distal plug or cap 15. Cutting ribs 14 may be assembled to, and driven by, a reamer handle 16 independently of centralizer 12. Rib assembly 10 includes cutting rib 14 in a rib frame 50, and centralizer 12 providing support for cutting rib 14. In some embodiments, cutting rib assembly 10 includes a stiff, unitized structure including a rib frame 50 having cutting ribs 14 and crossbar 13. Rib assembly 10 is terminated in a distal end with a cap or plug 15 being assembled to a frusto-conical end of centralizer 12. Reamer handle 16 may include a coupler 20 that firmly attaches to rib assembly 10. In some embodiments, coupler 20 may include a bayonet fitting configured to latch onto a crossbar 13 at the base of cutting rib 14. In some embodiments, reamer handle 16 includes a rotating shaft configured to provide a rotation motion to rib assembly 10, so that cutting rib 14 may chip away portions of a substrate when brought to contact with the substrate while rib assembly 10 is rotating. Attaching cutting ribs 14 to reamer handle 16 offers a number of advantages, such as reducing the potential for inducing compounded errors by reducing functional assembly tolerances, and eliminating additional deflections caused by moment forces and vibration induced through driving ribs through a medium.

In some embodiments, cutting rib 14 includes an arcuate portion 102 having an outer sharp edge 104. Outer sharp edge 104 protrudes outwardly from the surface of the centralizer. Arcuate portion 102 forms a window 106 having an inner edge 108. In some embodiments, inner edge 108 is configured to interlock with a second inner edge 108 of a second arcuate portion 102 of a second cutting rib 14, to form rib assembly 10. Centralizer 12 is configured to receive cutting rib 14 through a radial slot 12A, to form rib assembly 10, radial slot 12A forming a gap between cutting rib 14 and centralizer 12. In some embodiments, arcuate portion 102 of cutting rib 14 is formed into a profile that follows a surface of centralizer 12.

Figure 3:
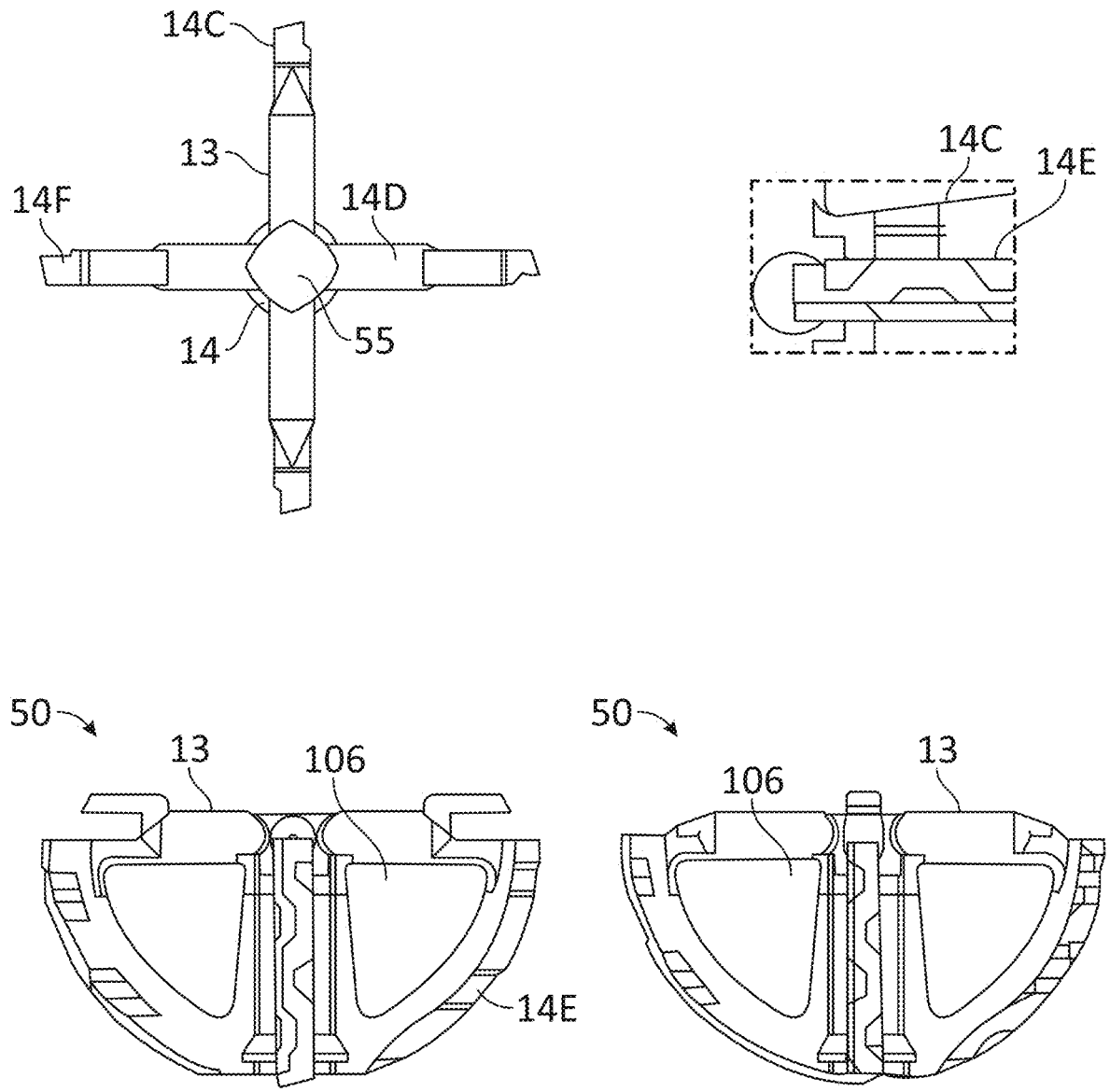
FIG. 3 illustrates views of a cutting rib with a rake, according to some embodiments.

FIG. 3 shows cutting rib 14 with a rake 14F. A rib frame 50 includes windows 106 that allow attachment to reamer handle 16 (cf. FIG. 2) via crossbar 13 on one end and joining at a central core 55. Cutting edge 14C and rake 14F are shown on an edge of each rib segment 14D, together with front view and cross-sections of tunnels 14E. Rake 14F is configured to gather debris from the substrate as the cutting rib rotates and contacts the substrate. Accordingly, in some embodiments, rake 14F is configured to move the debris into the inside portion of centralizer 12 (cf. FIG. 2).

Rake 14F may be pointed along the cutting face of cutting rib 14. A positive rake angle on each cutting face provides a number of benefits including making the tool more sharp and pointed. It would reduce cutting forces and power requirements. The addition of rake 14F promotes the formation of continuous chips (e.g., longer and bigger chip portions) in ductile bone materials. In some embodiments, rake 14F helps to avoid the formation of a built-up edge in sclerotic bone.

Figure 4:
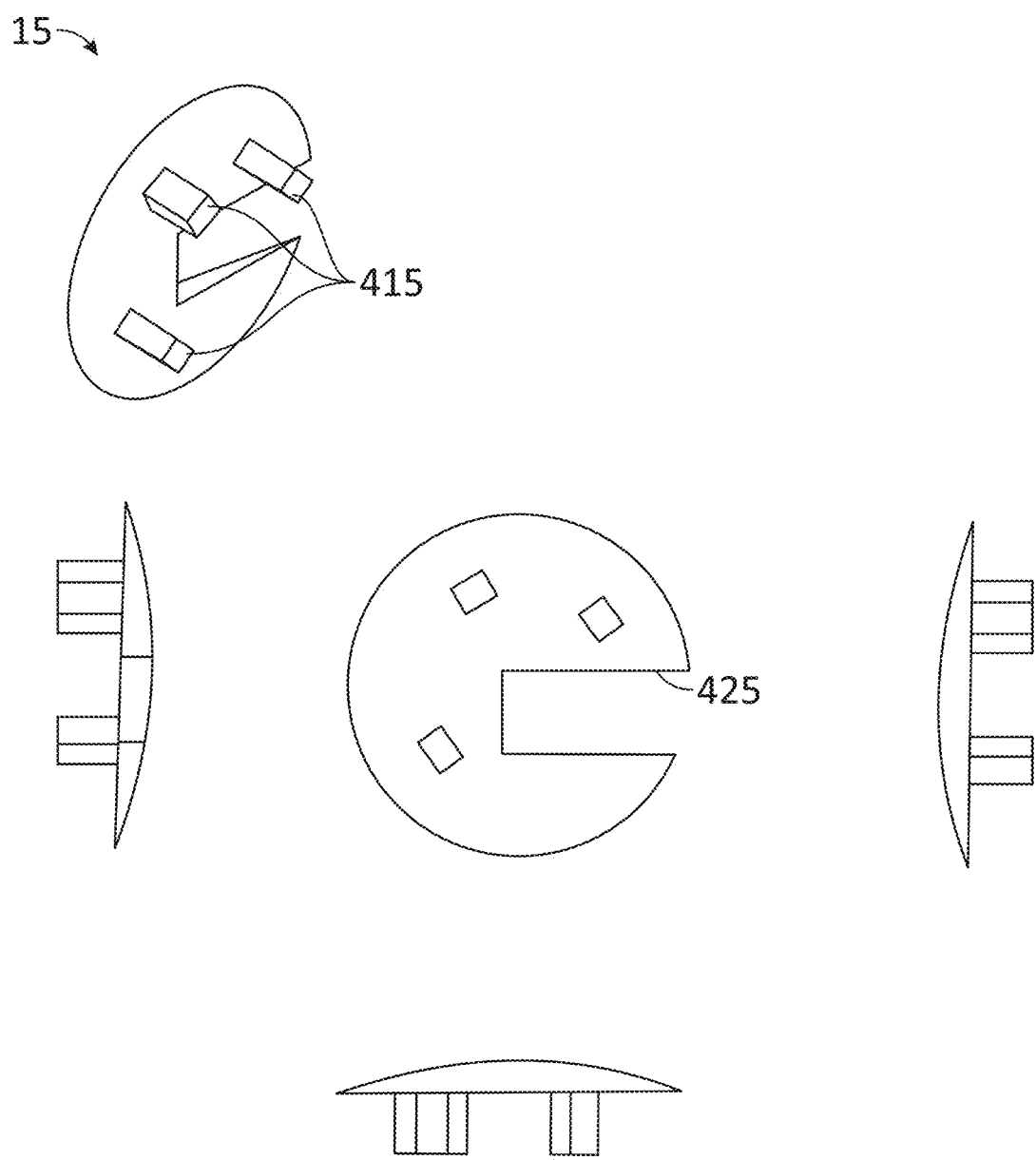
FIG. 4 depicts different views of a one-piece cap or plug used in connection with embodiments of a centralizer, according to some embodiments.

FIG. 4 shows one-piece cap or plug 15. Cap 15 limits the access of the distal parts of the cutting ribs 14 to the substrate (e.g., bone tissue) so that the cutting ribs will not be able to cut the substrate in that area. Accordingly, the substrate may be preserved where cap 15 covers the ribs. In some embodiments, cap 15 may include pins 415 and a notch 425. Pins 415 are disposed so that they secure the position of cap 15 at the tip of rib assembly 10 as the assembly is rotated. For example, pins 415 may be disposed so that a pressure fit within radial slots 12A maintains cap 15 in position. In some embodiments, at least one of pins 415 may fit inside a hole made on centralizer 12. Notch 425 allows residual material accumulating at the tip of cutting rib assembly 10, from the substrate, to transit to the inside, hollow side of centralizer 12, thus clearing the cutting surface/substrate interface of the assembly. Accordingly, cap 15 reduces friction between central core 55 and the substrate. This may be particularly helpful because central core 55 in rib frame 50 has a low speed relative to the substrate, as it is at the center of the rotation axis of cutting rib assembly 10. For example, in medical applications, cap 15 may protect the acetabular socket of the pelvis from unnecessary damage and stress during the reaming operation. After use, cap 15 may be removed, refurbished, replaced, or re-polished.

Figure 5:
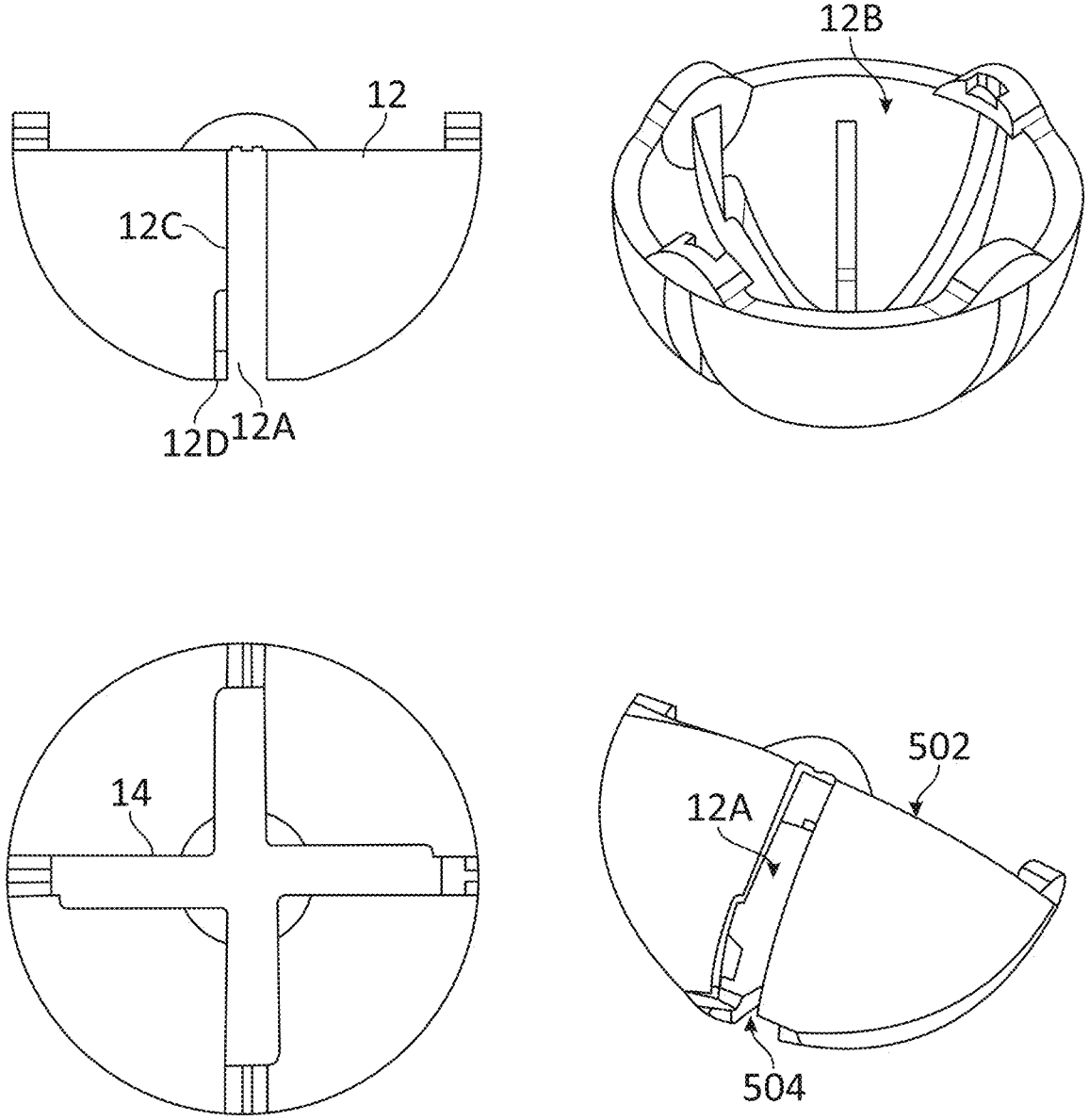
FIG. 5 illustrates views of a centralizer and radial slots for fitting cutting ribs in a cutting rib assembly, according to some embodiments.

FIG. 5 shows views of centralizer 12 and radial slots 12A for fitting cutting ribs in a cutting rib assembly, according to some embodiments. For illustrative purposes only, centralizer 12 is shown as a concave, hemispherical surface. Centralizer 12 includes a proximal opening 502, a distal opening 504, and a radial slot 12A. As cutting rib 14 rotates, it will push on only one of the sides (e.g., side 12C) of radial slot 12A so to turn centralizer 12. The open rail 12D will provide a passageway for bone chips and cartilage into the concave shape of the centralizer 12B. The substrate debris (e.g., bone chips) are collected inside and can later be used to correct and cure bone deficiencies.

Figure 6:
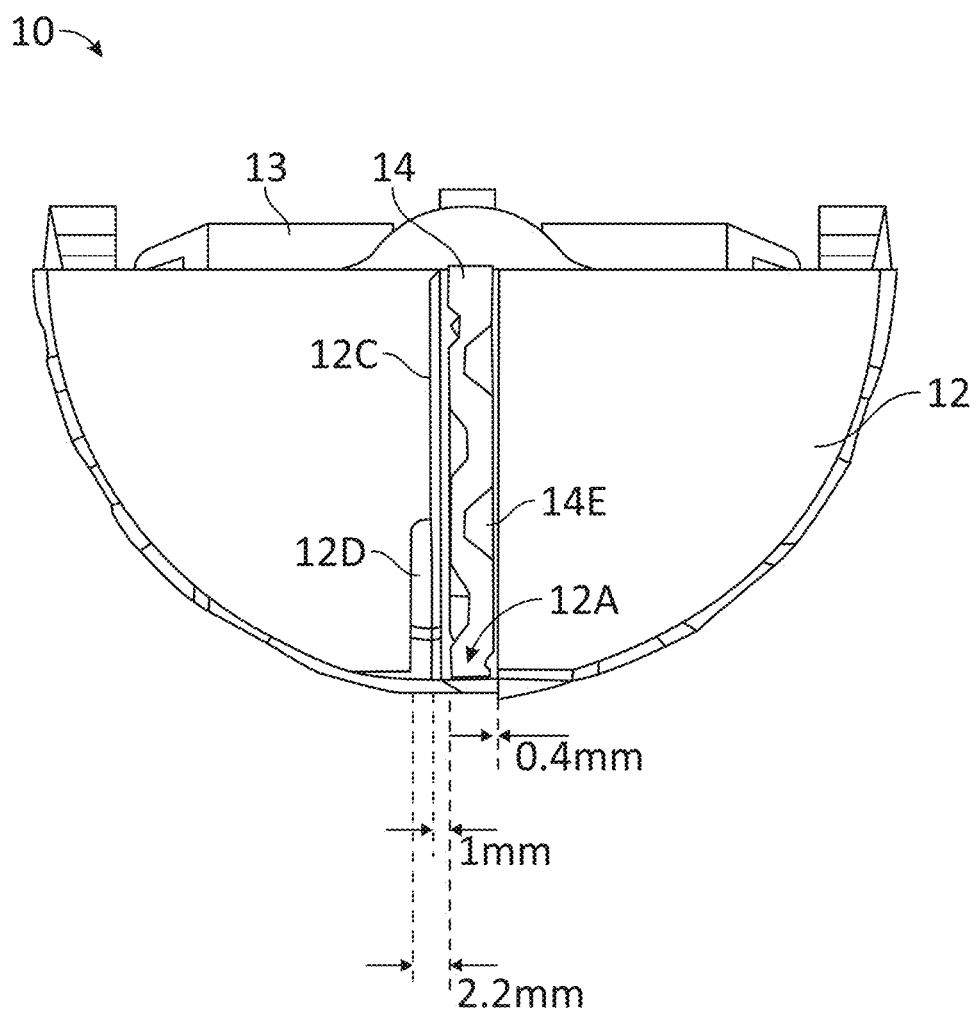
FIG. 6 depicts exemplary clearances between railing and ribs, according to some embodiments.

FIG. 6 shows a partial view of cutting rib assembly 10 with centralizer 12, illustrating a clearance between the centralizer 12 and cutting rib 14 (e.g., railing and rib) provided by radial slot 12A. The clearance on side 12C (e.g., 1 mm) between centralizer 12 and cutting rib 14 from radial slot 12A prevents contact between centralizer 12 and cutting rib 14. As seen, open rail 12D provides ample radial clearance (e.g., 2.2 mm) around cutting rib 14 to assure load and vibration are not carried from one rib onto other. Crossbar 13 and tunnels 14E are shown for completeness.

Figures 7A, 7B:
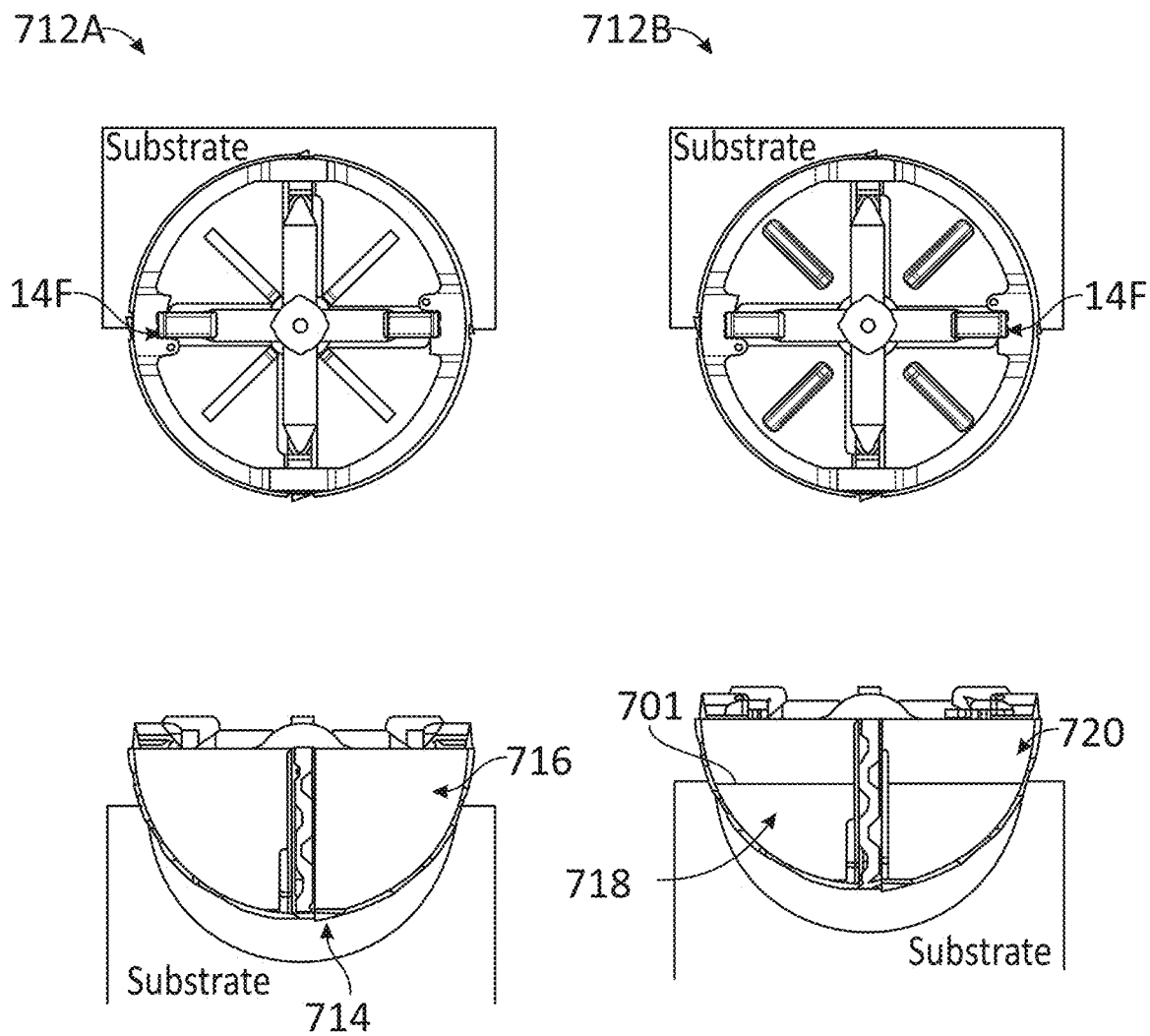
FIG. 7A illustrates views of a centralizer that is shown as substantially hemispherical, according to some embodiments.
FIG. 7B illustrates views of a centralizer with a multi-curved profile, according to some embodiments.

FIG. 7A shows a partially hemispherical centralizer 712A including a frusto-conical surface portion 714 and a spherical surface portion 716 with a proximal and distal opening. The frusto-conical portion 714 further reduces the amount that sharp edge of the ribs are allowed to embed into bone upon first contact with bone and thereafter with bone proximal to that contact zone. Rake 14F is shown in a top down view of centralizer 712A for illustrative purposes.

FIG. 7B shows a partially hemispherical centralizer 712B including a multi-curve surface portion, according to some embodiments. Centralizer 712B includes a partially hemispherical hollow body of appropriate thickness (usually less than 5 mm thick) with a proximal portion 720 and a distal portion 718. In some embodiments, distal portion 718 includes a frusto-conical segment and proximal portion 720 includes a spherical surface portion. The frusto-conical segment further reduces the amount that a sharp edge of cutting rib 14 embeds into the substrate upon first contact and thereafter.

A proximal portion 720 and a distal portion 718 in centralizer 712B follow different curvature radii. Proximal portion 720 joins distal portion 718 along a juncture 701. In some embodiments, a smaller radius of curvature in distal portion 718 reduces the amount that sharp edge of the ribs are allowed to embed into the substrate (e.g., bone) upon first contact and thereafter with substrate proximal to that contact zone. In some embodiments, the radius of curvature of distal portion 718 may be larger than the radius of curvature of proximal portion 720, to increase the reach depth of cutting rib 14 into the substrate. Rake 14F is shown in a top down view of centralizer 712B for illustrative purposes.

While centralizer 712B includes proximal portion 720 and distal portion 718, there is no limitation as the number of portions that may be included in a centralizer, according to some embodiments. For example, a centralizer in a cutting rib assembly as disclosed herein may include three, four, or more concave portions, each following a different radius of curvature. Moreover, in some embodiments, a centralizer as disclosed herein may include a single portion having a concave surface that is at least partially aspheric (non-spherical, e.g., parabolic, elliptic, or other).

FIGS. 8A-C illustrate views of centralizers 812A, 812B, and 812C (hereinafter, collectively referred to as "centralizers 812"), respectively, in several configurations of multi-curve profiles, according to some embodiments. Centralizers 812 include distal portions 818 and proximal portions 820, having different profiles, determined by a first radius of curvature 851a, 851b, and 851c (hereinafter, collectively referred to as "radii 851"), respectively. Distal portions 818 and proximal portions 820 are joined along juncture 801. Radii 851 are defined over a circle (or sphere) centered at a first point 861a, 861b, and 861c (hereinafter, collectively referred to as "centers 861"), respectively.

FIG. 8A shows proximal portion 820 following a second radius of curvature 852a for a sphere centered at point 862a. Point 862a is located slightly above point 861a, along axis A.

FIG. 8B shows proximal portion 820 following a second radius of curvature 852b for a sphere centered at point 862b. Point 862b is located to the side of point 861b, along a line perpendicular to axis A.

FIG. 8C shows proximal portion 820 following a straight line 854 making an angle 864 (α) relative to axis A.

Figure 9A:
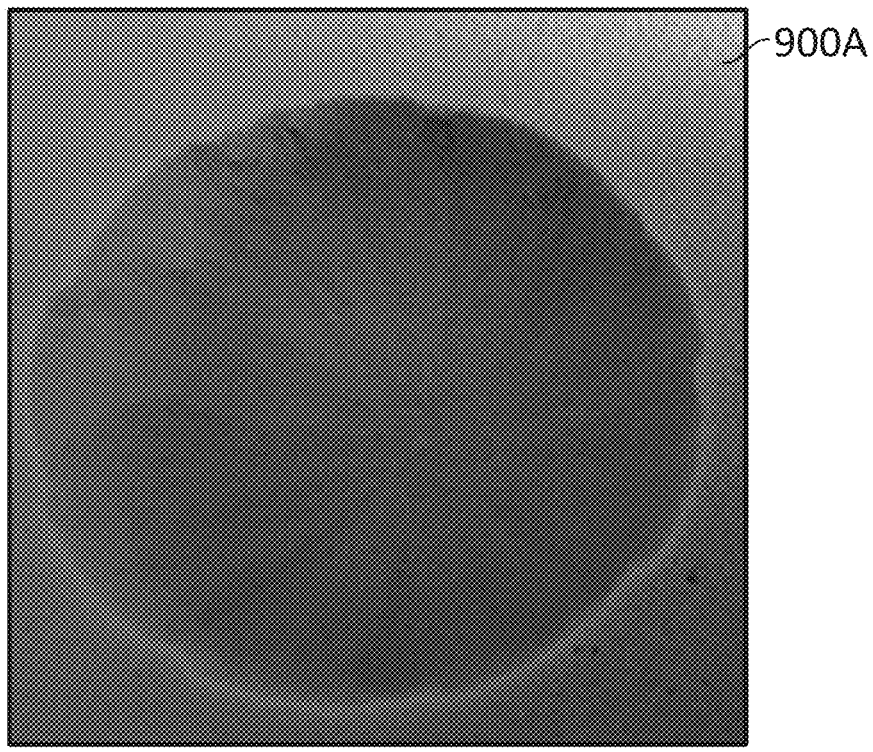
FIG. 9A shows a hemisphere reamed by a cutting rib assembly using a hemispherical centralizer, according to some embodiments.

FIG. 9A shows a hemisphere reamed on a substrate 900A by a cutting rib assembly using a hemispherical centralizer 12, according to some embodiments. For exemplary purposes only, the cutting rib assembly used on substrate 900A may include a single, hemispherical centralizer 12. Accordingly, a degree of unevenness is perceivable along the perimeter of the material.

Figure 9B:
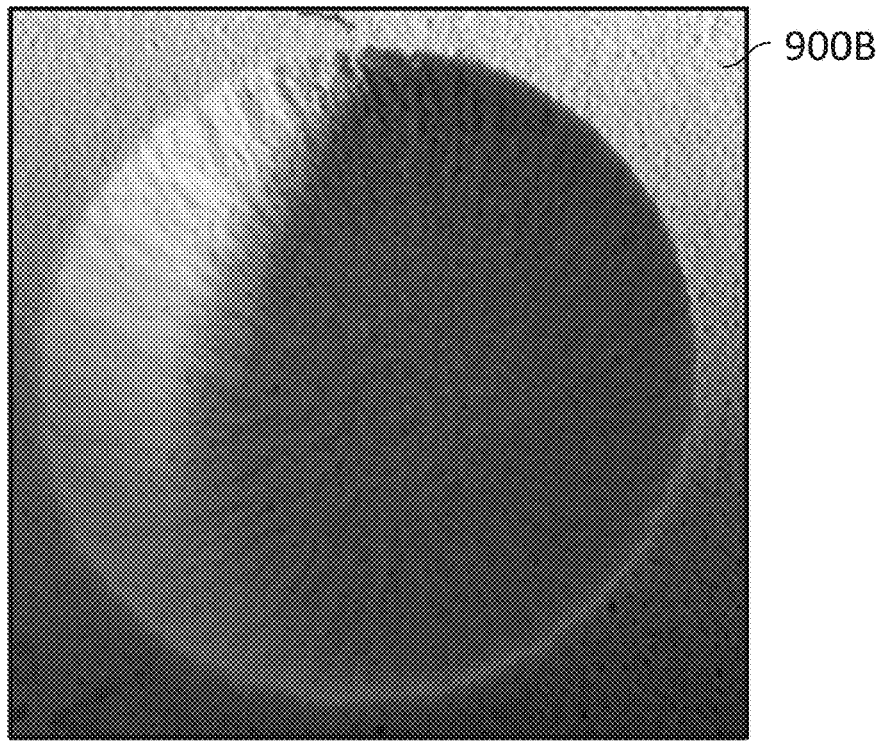
FIG. 9B shows a hemisphere reamed by a cutting rib assembly using a multi-concave centralizer, according to some embodiments.

FIG. 9B shows a hemisphere reamed on a substrate 900B by a blade reamer with a cutting rib assembly using a multi-concave centralizer, according to some embodiments. In some embodiments, a multi-concave centralizer may be as centralizer 712B (cf. FIG. 7B). It can be appreciated that the circular perimeter of the cut in substrate 900B is more clearly defined and smooth than that in substrate 900A.

Figure 10:
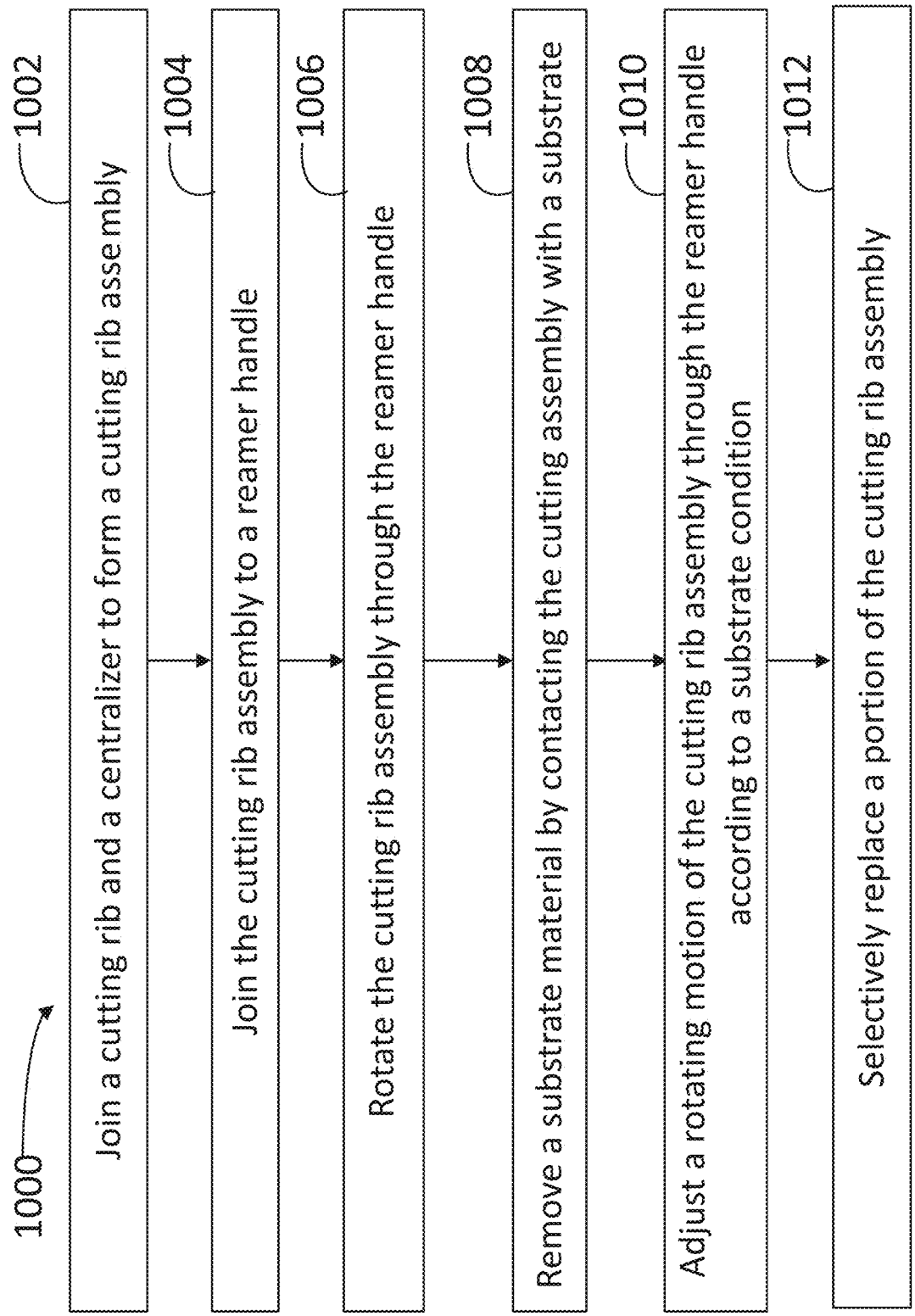
FIG. 10 illustrates a flow chart including steps in a method for removing a substrate material using a tool, according to some embodiments.

FIG. 10 illustrates a flow chart including steps in a method 1000 for removing a substrate material using a tool, according to some embodiments. In some embodiments, steps in method 900 may be used in conjunction with a surgical tool for cutting bone. The surgical tool may include a cutting rib assembly having cutting ribs, a centralizer, and a cap (e.g., cutting rib assembly 10, cutting ribs 14, and cap 15). Further, in some embodiments, the surgical tool may include a reamer handle (e.g., reamer handle 16) to provide a rotating motion to the cutting rib assembly, and the reamer handle may be coupled with the cutting rib assembly through a crossbar (e.g., crossbar 13).

Further, according to some embodiments, methods consistent with method 1000 may include at least one, but not all, of the steps illustrated in FIG. 10. Moreover, in some embodiments, a method as disclosed herein may include steps in method 1000 performed in a different sequence than that illustrated in FIG. 10. For example, in some embodiments, at least two or more of the steps in method 1000 may be performed overlapping in time, or even simultaneously, or quasi-simultaneously.

Step 1002 includes joining the cutting rib and the centralizer to form the cutting rib assembly. In some embodiments, step 1002 may include adjusting a crossbar in the cutting rib to protrude beyond the centralizer and form a proximal end of the cutting rib assembly.

Step 1004 includes joining the cutting rib assembly to the reamer handle. In some embodiments, step 1004 may include joining a distal end of the reamer handle with a proximal end of the cutting rib assembly. Accordingly, in some embodiments, the distal end of the reamer handle is configured to firmly grab the crossbar in the cutting rib.

Step 1006 includes rotating the cutting rib assembly through the reamer handle. In some embodiments, to ease cutting the bone, surgeons use powered reamer drivers. Some reamer drivers can spin as fast as 750 revolutions per minute (RPM). In some embodiments, a preferred rotational speed of reamers and tools as disclosed herein may be 350 RPM, or even lower than 350 RPM. More generally, surgeons may use reamers and tools as disclosed herein at speeds between about 350 RPM and about 750 RPM. At such speeds, debris may be effectively removed from the cutting surface of the rib and the cavity; otherwise, cutting debris may clog the cutting edge and hinder cutting and advancement of the reamer. When the slot in the centralizer is in close proximity or attached to the cutting rib, it would then hinder the passage of bone chips into the centralizer. In some embodiments, slots may be sufficiently separated along a radial direction from the cutting edge to allow the passage of soft tissue, cartilage, and bone chips through the slot.

Step 1008 includes removing a substrate material by contacting the cutting assembly with a substrate. In some embodiments, step 708 includes bringing the cutting rib assembly into contact with a substrate to remove substrate material.

Step 1010 includes adjusting the rotating motion of the cutting rib assembly through the reamer handle according to a substrate condition. In some embodiments, step 1010 may include measuring the temperature of the substrate. When reaming bone, friction between the cutter edge and bone generates heat. Following bone surgery, healing may be delayed or even prevented when the bone cells are injured by thermal necrosis resulting from frictional heat generated during surgical preparation. It is generally accepted that the critical level at which thermal necrosis appears in bone is when the bone is exposed to a temperature of around 56° C., over a time span exceeding 10 seconds. At this temperature the denaturation point of alkaline phosphatase is reached, which means that the change in properties are directly attributed to the reorientation of collagen molecules and hydroxyapatite. In some embodiments, reamers under constant load and RPM generate more heat than new reamers and temperatures exceeding 56° C. after a few times of use (e.g., about six or more).

Accordingly, in some embodiments, step 1010 may include reducing a rotating speed of the cutting rib assembly when the temperature of the substrate rises above a desirable level. Likewise, in some embodiments, step 1010 may include increasing the rotating speed of the cutting rib assembly when a harder portion of the substrate is reached. In some embodiments, step 1010 includes adjusting a cutting angle of the cutting rib assembly relative to the substrate (e.g., an axis normal to a plane tangential to the substrate's surface). For example, in some embodiments, step 1010 may include adjusting the cutting angle when a centralizer has multiple portions having different radii of curvature (e.g., centralizer 712B). Accordingly, step 1010 may include adjusting the cutting angle to contact the substrate with a selected one of the multiple portions having a selected radius of curvature (e.g., depth of cut into the substrate).

Step 1012 includes selectively replacing a portion of the cutting rib assembly. In some embodiments, step 1012 may include removing the cutting rib from the cutting rib assembly, to perform at least one of cleaning the cutting rib, re-tooling the cutting rib, or replacing the cutting rib. In some embodiments, step 1012 includes verifying that a sharpness of the cutting rib assembly surpasses a pre-selected threshold quality. In some embodiments, step 1012 may include detaching the cutting rib from the centralizer to remove portions of tissue (e.g., bone tissue, cartilage, and the like) from the cutting rib, the centralizer, or both, and grafting the removed portions of tissue back into the bone or other patient's tissue. In some embodiments, step 1012 may further include collecting and storing the removed portions of tissue for biopsy analysis or disposal. In some embodiments, step 1012 may further include forming a shape in a bone for receiving an implant by cutting bone with the cutting rib assembly. In some embodiments, step 1012 includes disposing a cap on a distal end of the cutting rib assembly to protect a slow moving tip of the cutting rib relative to the substrate, from the substrate.

Multiple variations and modifications are possible and consistent with embodiments disclosed herein. Although certain illustrative embodiments have been shown and described here, a wide range of modifications, changes, and substitutions is contemplated in the foregoing disclosure. While the above description contains many specifics, these should not be construed as limitations on the scope of the embodiment, but rather as exemplifications of one or another preferred embodiment thereof. In some instances, some features of the present embodiment may be employed without a corresponding use of the other features. Accordingly, it is appropriate that the foregoing description be construed broadly and understood as being given by way of illustration and example only, the spirit and scope of the embodiment being limited only by the appended claims.

What is claimed is:

1. A method, comprising:
    joining a cutting rib and a centralizer to form a cutting rib assembly;
    joining the cutting rib assembly to a reamer handle;
    rotating the cutting rib assembly through the reamer handle;
    removing a substrate material by contacting the cutting rib assembly with a substrate;
    adjusting a rotating motion of the cutting rib assembly through the reamer handle based on a substrate condition; and
    selectively replacing a portion of the cutting rib assembly.

2. The method of claim 1, wherein the substrate condition comprises a hardening of the substrate, and adjusting a rotating motion of the cutting rib assembly comprises increasing a rotating speed.

3. The method of claim 1, wherein adjusting a rotating motion of the cutting rib assembly comprises adjusting a cutting angle of the cutting rib assembly relative to the substrate.

4. The method of claim 1, wherein selectively replacing a portion of the cutting rib assembly comprises verifying that a sharpness of the cutting rib assembly is larger than a preselected threshold quality.

5. The method of claim 1, further comprising disposing a cap on a distal end of the cutting rib assembly to prevent the cutting rib from further advancing into the substrate, and only allowing radial cutting of material in a region proximal to the cap.

6. The method of claim 1, wherein the cutting rib comprises an arcuate portion having an outer sharp edge and removing a substrate material comprises contacting the outer sharp edge with a substrate.

7. The method of claim 1, further comprising coupling the cutting rib with the centralizer through a radial slot and forming a rib assembly, the radial slot forming a gap with the cutting rib.

8. The method of claim 1, further comprising forming a rib assembly with at least two interlocked cutting ribs.

9. The method of claim 1, wherein an outer surface of the centralizer comprises a multiple of radii.

10. The method of claim 1, further comprising avoiding a contact between the centralizer and a rib segment with a railing that provides a clearance between the centralizer and the rib segment.

11. The method of claim 1, further comprising gathering, within the centralizer, debris from a substrate as the cutting rib rotates and contacts the substrate with a rake on an end of an arcuate portion of the cutting rib.

12. The method of claim 1, further comprising firmly attaching the cutting rib assembly to a coupler of the reamer handle through a crossbar at a proximal end of the cutting rib.

13. The method of claim 1, further comprising rotating the cutting rib assembly with a rotating shaft of the reamer handle.

14. The method of claim 1, wherein joining a cutting rib and a centralizer comprises joining the cutting rib to a first portion of the centralizer consistent with a first spherical surface having a first radius.

15. The method of claim 1, further comprising disposing a cap in a distal tip of the centralizer to limit access of a distal portion of the cutting rib to a substrate.

16. The method of claim 1, further comprising securing a cap to a distal tip of the centralizer with at last one pin, as the cutting rib rotates against a substrate.

17. The method of claim 1, further comprising allowing debris from the substrate into an inner portion of the centralizer through a notch in a cap disposed on a distal tip of the centralizer, as the cutting rib rotates against the substrate.

* * * * *